(12) United States Patent
Kinoshita et al.

(10) Patent No.: US 9,465,288 B2
(45) Date of Patent: Oct. 11, 2016

(54) SULFONIUM SALT COMPOUND, METHOD FOR PRODUCING THE SAME, AND PHOTOACID GENERATOR

(71) Applicant: DSP GOKYO FOOD & CHEMICAL CO., LTD., Osaka-shi, Osaka (JP)

(72) Inventors: Hironori Kinoshita, Osaka (JP); Sumitsugu Kisanuki, Osaka (JP); Masaaki Sugi, Osaka (JP)

(73) Assignee: DSP GOKYO FOOD & CHEMICAL CO., LTD., Osaka (JP)

( * ) Notice: Subject to any disclaimer, the term of this patent is extended or adjusted under 35 U.S.C. 154(b) by 0 days.

(21) Appl. No.: 14/648,655

(22) PCT Filed: Dec. 3, 2013

(86) PCT No.: PCT/JP2013/082471
§ 371 (c)(1),
(2) Date: May 29, 2015

(87) PCT Pub. No.: WO2014/087998
PCT Pub. Date: Jun. 12, 2014

(65) Prior Publication Data
US 2015/0293445 A1   Oct. 15, 2015

(30) Foreign Application Priority Data
Dec. 7, 2012   (JP) ................... 2012-268078

(51) Int. Cl.
*G03F 7/004* (2006.01)
*C07C 381/00* (2006.01)
*C07C 311/48* (2006.01)
*C07C 381/12* (2006.01)
*G03F 7/039* (2006.01)
*C07D 285/15* (2006.01)

(52) U.S. Cl.
CPC ......... *G03F 7/0045* (2013.01); *C07C 311/48* (2013.01); *C07C 381/00* (2013.01); *C07C 381/12* (2013.01); *C07D 285/15* (2013.01); *G03F 7/039* (2013.01)

(58) Field of Classification Search
CPC ... G03F 7/0045; G03F 7/039; C07C 381/00; C07C 381/12; C07C 311/48; C07D 285/15
See application file for complete search history.

(56) References Cited

U.S. PATENT DOCUMENTS

| | | | |
|---|---|---|---|
| 3,205,157 A | 9/1965 | Licarie et al. | |
| 3,981,897 A | 9/1976 | Crivello | |
| 4,058,400 A | 11/1977 | Crivello | |
| 4,058,401 A | 11/1977 | Crivello | |
| 4,069,055 A | 1/1978 | Crivello | |
| 4,069,056 A | 1/1978 | Crivello | |
| 4,136,102 A | 1/1979 | Crivello | |
| 4,150,988 A | 4/1979 | Crivello | |
| 4,161,405 A | 7/1979 | Crivello | |
| 4,161,478 A | 7/1979 | Crivello | |
| 4,173,551 A | 11/1979 | Crivello | |
| 4,175,963 A | 11/1979 | Crivello | |
| 4,175,972 A | 11/1979 | Crivello | |
| 4,175,973 A | 11/1979 | Crivello | |
| 4,192,924 A | 3/1980 | Crivello | |
| 4,219,654 A | 8/1980 | Crivello | |
| 4,234,732 A | 11/1980 | Crivello | |
| 4,250,311 A | 2/1981 | Crivello | |
| 4,273,668 A | 6/1981 | Crivello | |
| 4,283,312 A | 8/1981 | Crivello | |
| 4,329,306 A | 5/1982 | Crivello | |
| 4,407,759 A | 10/1983 | Crivello | |
| 4,417,061 A | 11/1983 | Crivello | |
| 7,005,231 B2 * | 2/2006 | Tamaki | G02B 6/122 402/270.1 |
| 2004/0197698 A1 * | 10/2004 | Tamaki | G02B 6/122 430/270.1 |
| 2004/0229162 A1 * | 11/2004 | Ohsawa | C07C 381/12 430/270.1 |
| 2009/0068341 A1 | 3/2009 | Misumi et al. | |

FOREIGN PATENT DOCUMENTS

| | | |
|---|---|---|
| JP | S50-151997 A | 12/1975 |
| JP | H08-165290 A | 6/1996 |
| JP | 2004-334060 A | 11/2004 |
| JP | 2006-276755 A | 10/2006 |
| JP | 2007-171820 A | 7/2007 |
| JP | 2007-178621 A | 7/2007 |
| JP | 2010-256168 A | 11/2010 |
| WO | WO 03-010603 A | 2/2003 |

* cited by examiner

*Primary Examiner* — Shailendra Kumar
(74) *Attorney, Agent, or Firm* — Knobbe, Martens, Olson & Bear LLP

(57) ABSTRACT

Provided is a sulfonium salt compound represented by the following general formula (I):

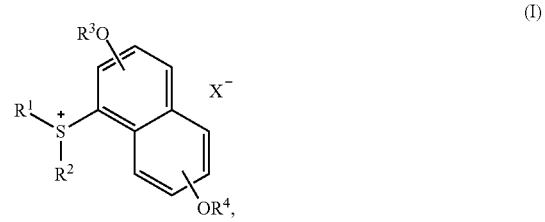

where $R^1$ and $R^2$ each denote the same or a different alkyl group having 1 to 18 carbon atoms, $R^3$ and $R^4$ each denote the same or a different alkyl group having 1 to 10 carbon atoms, and $X^-$ denotes a sulfone imide anion or a perfluoroalkanesulfonic acid anion, wherein the substituents denoted by $R^3O$ and $R^4O$ are each located at an arbitrary position selected from the 2-position to the 8-position of the naphthyl group.

7 Claims, No Drawings

SULFONIUM SALT COMPOUND, METHOD FOR PRODUCING THE SAME, AND PHOTOACID GENERATOR

CROSS-REFERENCE TO RELATED APPLICATION

This application is a 371 of PCT/JP2013/082471, filed on Dec. 3, 2013, which claims priority to Japanese Patent Application No. 2012-268078, the disclosure of which is incorporated herein by reference in its entirety.

FIELD

The present invention relates to a novel sulfonium salt compound, a method for producing the sulfonium salt compound, and a photoacid generator containing the sulfonium salt.

BACKGROUND

Conventionally, sulfonium salt compounds have been used for various applications, such as for a photoacid generator to be used for chemically amplified resist materials. Such a chemically amplified resist material generally contains a resin whose solubility is changed by acid, a photoacid generator, and a solvent. The chemically amplified resist material after being applied is irradiated with radiation such as an electron beam and X-ray within a region of a desired pattern of the applied chemically amplified resist material. Thus, the photoacid generator generates an acid in response to the irradiated radiation, and the generated acid changes the solubility of the resin, which allows a resist pattern for creating an integrated circuit to be formed.

Further, diligently investigation has been made for developing new applications of photoresists using thick film resists or improving conventional products thereof, and there is a demand to form a pattern of such a thick film resist with high accuracy. In order to obtain a pattern of the thick film resist with high accuracy, there is a demand for a photoacid generator having high sensitivity to radiation and high compatibility with other components in the resist material.

I-line radiation at a wavelength of 365 nm is widely used for forming a thick resist pattern using a photoacid generator. One of the reasons for that is availability of light sources such as a high-pressure mercury lamp and a metal halide lamp that allow good emission intensity of i-line light despite its low cost. Recent widespread adoption of LED lamps with an emission wavelength in the i-line region (360 to 390 nm) also can be mentioned. For such reasons, the importance of such a photoacid generator having high responsiveness to i-line light is thought to increase further in the future.

Molecular extinction coefficient ($\epsilon$) at 365 nm (i-line) is one of indicators for responsiveness to i-line light. As a sulfonium salt compound used as a photoacid generator of this type, an aryldiazonium salt compound (Patent Literature 1), a triarylsulfonium salt compound (Patent Literature 2), and the like have been conventionally proposed. However, aryldiazonium salts and triarylsulfonic acid salts have a maximum absorption wavelength of 300 nm or less, and have a low molecular extinction coefficient ($\epsilon$) at 365 nm. Therefore, in the case of using a light source such as a high-pressure mercury lamp and a metal halide lamp, there are problems that acid generation efficiency is low, and a resist pattern with high accuracy is difficult to obtain.

On the other hand, an increase in molecular extinction coefficient ($\epsilon$) at 365 nm does not necessarily lead to an improvement in sensitivity. For example, a sulfonium salt compound into which a thioxanthone skeleton is introduced (Patent Literature 3) absorbs light mostly on the side of the surface on which the resist material is applied because of its excessively high molecular extinction coefficient ($\epsilon$) at 365 nm (i-line). As a result, the light is not transmitted to a deep portion, and thus the acid generation efficiency rather tends to decrease.

Further, most part of components of a chemically amplified resist material is a solvent. In particular, propylene glycol 1-monomethyl ether 2-acetate (PGMEA) is widely used as the solvent. Therefore, in order to obtain a photoacid generator having high compatibility with other components including such PGMEA, the solubility in PGMEA is very important. Patent Literatures 1 to 3 mentioned above propose $BF_4^-$, $PF_6^-$, $SbF_6^-$, or the like as an anion of the sulfonium salt compound that is used as a photoacid generator of a chemically amplified resist material. However, the sulfonium salt compound containing such an anion generally does not have sufficient solubility in PGMEA.

Therefore, a sulfonium salt compound having a naphthalene ring in a cationic part is, for example, proposed as being useful as a photoacid generator for a chemically amplified resist (see Patent Literatures 4 to 6).

CITATION LIST

Patent Literature

Patent Literature 1: U.S. Pat. No. 3,205,157
Patent Literature 2: JP S50-151997 A
Patent Literature 3: JP H8-165290 A
Patent Literature 4: JP 2004-334060 A
Patent Literature 5: JP 2006-276755 A
Patent Literature 6: JP 2010-256168 A

SUMMARY

Technical Problem

However, the aforementioned sulfonium salt compound having a naphthalene ring in a cationic part is not satisfactory in view of efficient acid generation in use for a thick film photoresist using i-line light (365 nm). The reasons for this include that the molecular extinction coefficient at 365 nm is not sufficiently suitable, the strength of acid to be generated is insufficient, and the solubility in PGMEA is insufficient, for example. Therefore, there is a demand for a further improvement in the sulfonium salt compound.

In view of the aforementioned problems, it is an object of the present invention to provide a novel sulfonium salt compound that generates acid more efficiently than conventional compounds and has good solubility in a solvent used for resist materials or the like, a method for producing the novel sulfonium salt compound, and a photoacid generator.

Solution to Problem

As a result of diligent studies in view of the aforementioned object, the inventors of the subject application have found that a sulfonium salt compound including a cation part having a sulfonium cation structure containing a specific naphthyl group and an anion part having a sulfone imide anion structure or a perfluoroalkanesulfonic acid anion structure has higher sensitivity particularly to i-line light than conventional compounds and sufficiently high solubility in a solvent used for chemically amplified resist materials or the like. Thus, the present invention has been accomplished.

That is, the sulfonium salt compound according to the present invention is represented by the following general formula (I):

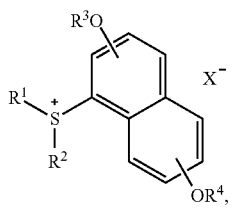
(I)

where $R^1$ and $R^2$ each denote the same or a different alkyl group having 1 to 18 carbon atoms, $R^3$ and $R^4$ each denote the same or a different alkyl group having 1 to 10 carbon atoms, and $X^-$ denotes a sulfone imide anion or a perfluoroalkanesulfonic acid anion, wherein the substituents denoted by $R^3O$ and $R^4O$ are each located at an arbitrary position selected from the 2-position to the 8-position of the naphthyl group.

Further, in the sulfonium salt compound of the present invention, it is preferable that $R^1$ and $R^2$ each denote the same or a different alkyl group having 1 to 8 carbon atoms, and $R^3$ and $R^4$ each denote the same or a different alkyl group having 1 to 8 carbon atoms.

Further, in the sulfonium salt compound of the present invention, it is preferable that $X^-$ denote a sulfone imide anion represented by the following general formula (II) or (III);

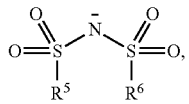
(II)

where $R^5$ and $R^6$ each denote the same or a different alkyl group having 1 to 6 carbon atoms in which at least one hydrogen atom is substituted by a fluorine atom; or

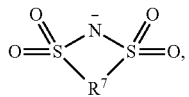
(III)

where $R^7$ denotes an alkylene group having 2 to 5 carbon atoms in which at least one hydrogen atom is substituted by a fluorine atom.

Further, in the sulfonium salt compound of the present invention, it is preferable that $R^5$ and $R^6$ each denote the same or a different alkyl group having 1 to 4 carbon atoms in which at least one hydrogen atom is substituted by a fluorine atom.

Further, in the sulfonium salt compound of the present invention, it is preferable that $R^7$ denote an alkylene group having 3 carbon atoms in which at least one hydrogen atom is substituted by a fluorine atom.

Further, in the sulfonium salt compound of the present invention, it is preferable that $X^-$ denote a perfluoroalkanesulfonic acid anion represented by the general formula (IV);

$$R^8-SO_3^- \quad (IV),$$

where $R^8$ denotes an alkyl group having 2 to 4 carbon atoms in which all hydrogen atoms are substituted by fluorine atoms.

A photoacid generator according to the present invention contains the aforementioned sulfonium salt compound.

A method for producing a sulfonium salt compound according to the present invention includes; Step (a) of subjecting, to dehydration condensation, a sulfoxide compound represented by the following general formula (V);

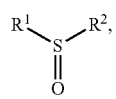
(V)

where $R^1$ and $R^2$ each denote the same or a different alkyl group having 1 to 18 carbon atoms, and a naphthalene compound represented by the following formula (VI);

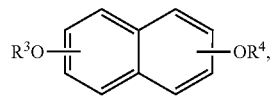
(VI)

where $R^3$ and $R^4$ each denote the same or a different alkyl group having 1 to 10 carbon atoms, wherein the substituents denoted by $R^3O$ and $R^4O$ are each located at an arbitrary position selected from the 2-position to the 8-position of the naphthyl group; and Step (b) of producing a sulfonium salt compound represented by the following general formula (I)

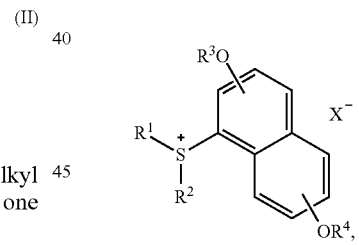
(I)

where $R^1$ and $R^2$ each denote the same substituent as defined in the aforementioned general formula (V), $R^3$ and $R^4$ each denote the same substituent as defined in the aforementioned general formula (VI), and $X^-$ denotes the same substituent as defined in the general formula $X^-Y^+$, by reaction between a dehydrated condensate obtained by the dehydration condensation in Step (a) and a salt compound or an acid compound represented by a general formula $X^-Y^+$, where $X^-$ is represented by the following general formula (II), (III), or (IV), and $Y^+$ denotes an alkali metal ion or a hydrogen ion:

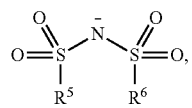
(II)

where $R^5$ and $R^6$ each denote the same or a different alkyl group having 1 to 6 carbon atoms in which at least one hydrogen atom is substituted by a fluorine atom;

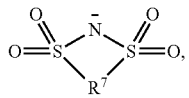

(III)

where $R^7$ denotes an alkylene group having 2 to 5 carbon atoms in which at least one hydrogen atom is substituted by a fluorine atom; or

 (IV), where $R^8$ denotes an alkyl group having 2 to 4 carbon atoms in which all hydrogen atoms are substituted by fluorine atoms.

DESCRIPTION OF EMBODIMENTS

Hereinafter, embodiments of the sulfonium salt compound according to the present invention are described.

The sulfonium salt compound of the present invention is represented by the following structural formula (I):

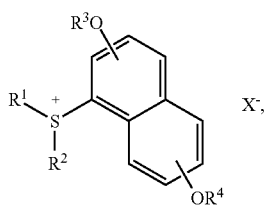

(I)

where $R^1$ and $R^2$ each denote the same or a different alkyl group having 1 to 18 carbon atoms, $R^3$ and $R^4$ each denote the same or a different alkyl group having 1 to 10 carbon atoms, and $X^-$ denotes a sulfone imide anion or a perfluoroalkanesulfonic acid anion, wherein the substituents denoted by $R^3O$ and $R^4O$ are each located at an arbitrary position selected from the 2-position to the 8-position of the naphthyl group.

The alkyl group having 1 to 18 carbon atoms may be straight-chained or branched-chained. Examples of the alkyl group include a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, and an octadecyl group. Among these, a butyl group is particularly preferable.

The substituents denoted by $R^1$ and $R^2$ are each preferably the same or a different alkyl group having 1 to 8 carbon atoms, more preferably the same or a different butyl group, particularly preferably a butyl group.

The substituents denoted by $R^3$ and $R^4$ are each preferably the same or a different alkyl group having 1 to 8 carbon atoms, more preferably the same or a different butyl group, particularly preferably a butyl group.

The substituents denoted by $R^3$ and $R^4$ are located at arbitrary positions selected from the 2-position to the 8-position of the naphthyl group. Among these, they are preferably located respectively at the 4-position and the 8-position, the 4-position and the 7-position, or the 2-position and the 7-position.

As mentioned above, the cation is particularly preferably dibutyl(4,8-dibutoxynaphthalene-1-yl)sulfonium cation, dibutyl(4,7-dibutoxynaphthalene-1-yl)sulfonium cation, or dibutyl(2,7-dibutoxynaphthalene-1-yl)sulfonium cation.

$X^-$ denotes a sulfone imide anion or a perfluoroalkanesulfonic acid anion. The sulfone imide anion is preferably a sulfone imide anion represented by the general formula (II) or (III);

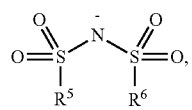

(II)

where $R^5$ and $R^6$ each denote the same or a different alkyl group having 1 to 6 carbon atoms in which at least one hydrogen atom is substituted by a fluorine atom; or

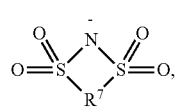

(III)

where $R^7$ denotes an alkylene group having 2 to 5 carbon atoms in which at least one hydrogen atom is substituted by a fluorine atom.

Examples of the alkyl group having 1 to 6 carbon atoms in which at least one hydrogen atom is substituted by a fluorine atom, which is denoted by $R^5$ and $R^6$ in the aforementioned general formula (II), include trifluoromethyl, pentafluoroethyl, heptafluoropropyl, nonafluorobutyl, and undecafluoropentyl. Among these, nonafluorobutyl is preferable. Further, it is particularly preferable that $R^5$ and $R^6$ mentioned above be each nonafluorobutyl.

Examples of the alkylene group having 2 to 5 carbon atoms, which is denoted by $R^7$ in the aforementioned general formula (III), include tetrafluoroethylene, hexafluoropropylene, octafluorobutylene, and decafluoropentylene. Among these, hexafluoropropylene is preferable. Further, it is particularly preferable that $R^7$ be an alkylene group having 3 carbon atoms in which at least one hydrogen atom is substituted by a fluorine atom.

Further, the perfluoroalkanesulfonic acid anion is, for example, preferably a perfluoroalkanesulfonic acid anion represented by the following general formula (IV):

 (IV), where $R^8$ denotes an alkyl group having 2 to 4 carbon atoms in which all hydrogen atoms are substituted by fluorine atoms.

Examples of the alkyl group having 2 to 4 carbon atoms in which all hydrogen atoms are substituted by fluorine atoms, which is denoted by $R^8$ in the aforementioned general formula (IV), include pentafluoroethyl, heptafluoropropyl, and nonafluorobutyl. Among these, it is particularly preferable that the aforementioned alkyl group be nonafluorobutyl.

Examples of the anion having such substituents as mentioned above, which is represented by $X^-$, include a bis (trifluoromethanesulfone)imide anion, a bis(pentafluoroethanesulfone)imide anion, a bis(heptafluoropropanesulfone) imide anion, a bis(nonafluorobutanesulfone)imide anion, a bis(undecafluoropentanesulfone)imide anion, a bis(tridecafluorohexanesulfone)imide anion, a trifluoromethane(pentafluoroethane)sulfone imide anion, a trifluoromethane(nonabutan)sulfone imide anion, a trifluoromethane(undecafluoropentane)sulfone imide anion, a trifluoromethane(tridecafluorohexane)sulfone imide anion, a pentafluoroethane(heptafluoropropane)sulfone imide anion, a pentafluoroethane(nonabutan)sulfone imide anion, a heptafluoropropane(nonabutan)sulfone imide anion, a pentafluoroethane(tridecafluorohexane)sulfone imide anion, a tetrafluoroethylene sulfone imide anion, a hexafluorotrimethylene sulfone imide anion, an octafluorotetramethylene sulfone imide anion, a decafluoropentamethylene sulfone imide anion, a pentafluoroethane sulfonate anion, a heptafluoropropane sulfonate anion, and a nonafluorobutanesulfonate anion. The word "bis" means that the number of substituents is two like the aforementioned word "di". The same applies also to the following description.

Among these, the anion represented by $X^-$ mentioned above is preferably a bis(nonafluorobutanesulfone)imide anion, a hexafluorotrimethylene sulfone imide anion, or a nonafluorobutanesulfonate anion.

From the above description, it is preferable that, in the sulfonium salt compound represented by the aforementioned chemical formula (I), $R^1$ and $R^2$ each denote the same or a different alkyl group having 1 to 8 carbon atoms, $R^3$ and $R^4$ each denote the same or a different alkyl group having 1 to 8 carbon atoms, the substituents denoted by $R^3$ and $R^4$ be respectively located at the 2-position and the 4-position, the 4-position and the 8-position, the 4-position and the 7-position, or the 2-position and the 7-position of the naphthyl group, $X^-$ be a sulfone imide anion represented by the aforementioned general formula (II), and $R^5$ and $R^6$ each denote an alkyl group having 1 to 6 carbon atoms in which at least one hydrogen atom is substituted by a fluorine atom.

Further, it is preferable that, in the sulfonium salt compound represented by the aforementioned chemical formula (I), $R^1$ and $R^2$ each denote the same or a different alkyl group having 1 to 8 carbon atoms, $R^3$ and $R^4$ each denote the same or a different alkyl group having 1 to 8 carbon atoms, the substituents denoted by $R^3$ and $R^4$ be respectively located at the 2-position and the 4-position, the 4-position and the 8-position, the 4-position and the 7-position, or the 2-position and the 7-position of the naphthyl group, $X^-$ be a sulfone imide anion represented by the aforementioned general formula (III), and $R^7$ denote an alkylene group having 2 to 5 carbon atoms in which at least one hydrogen atom is substituted by a fluorine atom.

Further, it is preferable that, in the sulfonium salt compound represented by the aforementioned chemical formula (I), $R^1$ and $R^2$ each denote the same or a different alkyl group having 1 to 8 carbon atoms, $R^3$ and $R^4$ each denote the same or a different alkyl group having 1 to 8 carbon atoms, the substituents denoted by $R^3$ and $R^4$ be respectively located at the 2-position and the 4-position, the 4-position and the 8-position, the 4-position and the 7-position, or the 2-position and the 7-position of the naphthyl group, $X^-$ be a perfluoroalkanesulfonic acid anion represented by the aforementioned general formula (IV), and $R^8$ be an alkyl group having 2 to 4 carbon atoms in which all hydrogen atoms are substituted by fluorine atoms.

Further, the sulfonium salt compound represented by the aforementioned chemical formula (I) is particularly preferably 1-(2,7-di-n-butoxynaphthyl)di-n-butylsulfonium di(1,1,2,2,3,3,4,4,4-nonafluorobutanesulfone)imide, 1-(4,7-di-n-butoxynaphthyl)di-n-butylsulfonium di(1,1,2,2,3,3,4,4,4-nonafluorobutanesulfone)imide, 1-(2,7-di-n-butoxynaphthyl)di-n-butylsulfonium 1,1,2,2,3,3-hexafluoropropylene imide, 1-(2,7-di-n-butoxynaphthyl)di-n-butylsulfonium 1,1,2,2,3,3,4,4,4-nonafluorobutanesulfonate, 1-(4,8-di-n-butoxynaphthyl)di-n-butylsulfonium di(1,1,2,2,3,3,4,4,4-nonafluorobutanesulfone)imide, 1-(4,8-di-n-butoxynaphthyl)di-n-butylsulfonium di(1,1,1-trifluoromethyl sulfone)imide, 1-(2,7-di-n-butoxynaphthyl) dimethylsulfonium di(1,1,2,2,3,3,4,4,4-nonafluorobutanesulfone)imide, or 1-(2,4-di-n-butoxynaphthyl)di-n-butylsulfonium di(1,1,2,2,3,3,4,4,4-nonafluorobutanesulfone)imide.

Subsequently, a method for producing the sulfonium salt compound represented by the aforementioned general formula (I) according to the present embodiment is described. This sulfonium salt compound is produced, for example, using a sulfoxide compound, a naphthalene compound, and a compound represented by $X^-Y^+$, which will be described below, as raw materials.

Specifically, the sulfoxide compound to be used for producing the sulfonium salt compound represented by the aforementioned chemical formula (I), for example, is represented by the following formula (V):

(V)

where $R^1$ and $R^2$ each denote the same or a different alkyl group having 1 to 18 carbon atoms, as mentioned above.

Specific examples of the sulfoxide compound represented by the aforementioned chemical formula (V) include diethylsulfoxide, dipropylsulfoxide, dibutylsulfoxide, dipentylsulfoxide, dihexylsulfoxide, diheptylsulfoxide, dioctylsulfoxide, dinonylsulfoxide, didodecylsulfoxide, isopropylmethylsulfoxide, methylpropylsulfoxide, butylethylsulfoxide, and methyloctylsulfoxide. Among these, the sulfoxide compound is preferably dibutylsulfoxide.

As the aforementioned sulfoxide compound, a commercially available sulfoxide compound may be used as it is, or an appropriately produced sulfoxide compound may be used. The method for producing such a sulfoxide compound is not specifically limited; for example, the sulfoxide compound can be produced with reference to a publicly known method such as methods disclosed in Tetrahedron, 57, 2469 (2001) and Molecules, 12, 304 (2007).

The naphthalene compound to be used for producing the sulfonium salt compound represented by the aforementioned chemical formula (I), for example, is represented by the following general formula (VI):

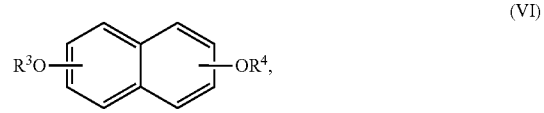

(VI)

where $R^3$ and $R^4$ each denote the same or a different alkyl group having 1 to 10 carbon atoms, as mentioned above, wherein the substituents denoted by $R^3O$ and $R^4O$ are each located at an arbitrary position selected from the 2-position to the 8-position of the naphthyl group.

As the naphthalene compound represented by the aforementioned general formula (VI), a commercially available naphthalene compound may be used as it is, or an appropriately produced naphthalene compound may be used. The method for producing such a naphthalene compound is not specifically limited; for example, the naphthalene compound can be produced with reference to a publicly known method such as methods disclosed in J. Comb. Chem., 6, 497 (2004) and J. Org. Chem., 70, 1115 (2005).

Examples of the naphthalene compound include 1,5-diethoxynaphthalene, 1,5-dipropoxynaphthalene, 1,5-diisopropoxynaphthalene, 1,5-dibutoxynaphthalene, 1-ethoxy-5-methoxynaphthalene, 1-methoxy-5-propoxynaphthalene, 1-isopropoxy-5-methoxynaphthalene, 1-butoxy-5-methoxynaphthalene, 1,6-diethoxynaphthalene, 1,6-dipropoxynaphthalene, 1,6-diisopropoxynaphthalene, 1,6-dibutoxynaphthalene, 6-ethoxy-1-methoxynaphthalene, 1-methoxy-6-propoxynaphthalene, 6-isopropoxy-1-methoxynaphthalene, 6-butoxy-1-methoxynaphthalene, 1,7-diethoxynaphthalene, 1,7-dipropoxynaphthalene, 1,7-diisopropoxynaphthalene, 1,7-dibutoxynaphthalene, 7-ethoxy-1-methoxynaphthalene, 1-methoxy-7-propoxynaphthalene, 7-isopropoxy-1-methoxynaphthalene, 7-butoxy-1-methoxynaphthalene, 2,7-diethoxynaphthalene, 2,7-dipropoxynaphthalene, 2,7-diisopropoxynaphthalene, 2,7-dibutoxynaphthalene, 2-ethoxy-7-methoxynaphthalene, 2-methoxy-7-propoxynaphthalene, 2-isopropoxy-7-methoxynaphthalene, and 2-butoxy-7-methoxynaphthalene. Among these, the aforementioned naphthalene compound is preferably 1,5-dibutoxynaphthalene, 1,6-dibutoxynaphthalene, 1,3-dibutoxynaphthalene, or 2,7-dibutoxynaphthalene.

The salt compound or acid compound to be used for producing the sulfonium salt compound represented by the aforementioned chemical formula (I) is represented by a general formula $X^-Y^+$, where $X^-$ is represented by the following general formula (II), (III) or (IV), as mentioned above, and $Y^+$ denotes an alkali metal ion or a hydrogen ion:

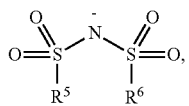   (II)

where $R^5$ and $R^6$ each denote the same or a different alkyl group having 1 to 6 carbon atoms in which at least one hydrogen atom is substituted by a fluorine atom, as mentioned above,

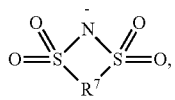   (III)

where $R^7$ denotes an alkylene group having 2 to 5 carbon atoms in which at least one hydrogen atom is substituted by a fluorine atom, as mentioned above, or $$R^8-SO_3^-\quad\text{(IV),}$$

where $R^8$ denotes an alkyl group having 2 to 4 carbon atoms in which all hydrogen atoms are substituted by fluorine atoms, as mentioned above.

Examples of the $X^-$ having such substituents include the aforementioned anions.

Further, in the case where $Y^+$ is an alkali metal ion, examples of $Y^+$ include a lithium cation, a sodium cation, and a potassium cation, in view of the reactivity.

That is, examples of the aforementioned $X^-Y^+$ include alkali metal salts such as sodium salts, potassium salts, and lithium salts of the aforementioned $X^-$ anions, and acids represented by $X^-H^+$. $X^-Y^+$ is preferably the alkali metal salts because of their excellent reactivity.

Examples of the salt compound represented by the aforementioned general formula $X^-Y^+$ include lithium bis(trifluoromethanesulfone)imide, sodium bis(trifluoromethanesulfone)imide, potassium bis(trifluoromethanesulfone)imide, lithium bis(pentafluoroethanesulfone)imide, lithium bis(heptafluoropropanesulfone)imide, potassium bis(nonafluorobutanesulfone)imide, lithium bis(nonafluorobutanesulfone)imide, lithium bis(undecafluoropentanesulfone)imide, potassium bis(tridecafluorohexanesulfone)imide, lithium trifluoromethane(pentafluoroethane)sulfone imide, potassium trifluoromethane(pentafluoroethane)sulfone imide, potassium trifluoromethane(nonabutan)sulfone imide, lithium trifluoromethane(nonabutan)sulfone imide, lithium trifluoromethane(undecafluoropentane)sulfone imide, lithium trifluoromethane(tridecafluorohexane)sulfone imide, potassium pentafluoroethane(heptafluoropropane)sulfone imide, lithium pentafluoroethane(nonabutan)sulfone imide, potassium heptafluoropropane(nonabutan)sulfone imide, potassium pentafluoroethane(tridecafluorohexane)sulfone imide, lithium tetrafluoroethylene sulfone imide, lithium hexafluorotrimethylene sulfone imide, potassium hexafluorotrimethylene sulfone imide, lithium octafluorotetramethylene sulfone imide, lithium decafluoropentamethylene sulfone imide, potassium pentafluoroethane sulfonate, potassium heptafluoropropane sulfonate, lithium nonafluorobutanesulfonate, and potassium nonafluorobutanesulfonate.

Further, examples of the acid compound represented by the aforementioned general formula $X^-Y^+$ include bis(trifluoromethanesulfone)imide, bis(pentafluoroethanesulfone)imide, bis(heptafluoropropanesulfone)imide, bis(nonafluorobutanesulfone)imide, bis(undecafluoropentanesulfone)imide, bis(tridecafluorohexanesulfone)imide, trifluoromethane(pentafluoroethane)sulfone imide, trifluoromethane(nonabutan)sulfone imide, trifluoromethane(undecafluoropentane)sulfone imide, trifluoromethane(tridecafluorohexane)sulfone imide, pentafluoroethane (heptafluoropropane)sulfone imide, pentafluoroethane (nonabutan)sulfone imide, heptafluoropropane(nonabutan)sulfone imide, pentafluoroethane(tridecafluorohexane)sulfone imide, tetrafluoroethylene sulfone imide, hexafluorotrimethylene sulfone imide, octafluorotetramethylene sulfone imide, decafluoropentamethylene sulfone imide, pentafluoroethane sulfonate, heptafluoropropane sulfonate, and nonafluorobutanesulfonate. Among these, potassium bis(nonafluorobutanesulfone)imide, lithium bis(nonafluorobutanesulfone)imide, lithium hexafluorotrimethylene sulfone imide, potassium hexafluorotrimethylene sulfone imide, lithium nonafluorobutanesulfonate, and potassium nonafluorobutanesulfonate are preferable.

As the compound represented by the aforementioned general formula $X^-Y^+$, a commercially available compound may be used as it is, or an appropriately produced compound may be used. The method for producing the $X^-Y^+$ compound is not specifically limited; for example, the $X^-Y^+$ compound can be produced with reference to a publicly known method such as methods disclosed in Inorg. Chem., 23, 3720 (1984), Inorg. Chem., 32, 5007 (1993), J. Fluorine Chem., 125, 243 (2004), and Eur. J. Inorg. Chem., 22, 3419 (2010).

Further, in the case where the alkali metal salt is not commercially available, the alkali metal salt can be produced, for example, by neutralizing an aqueous solution of a commercially available acid represented by $X^-H^+$ with sodium hydroxide, potassium hydroxide, lithium hydroxide, or the like. In this neutralization, a hydrogen ion is converted into the aforementioned alkali metal ion. Further, the thus obtained aqueous solution of the alkali metal salt can be used as it is in the later-mentioned step (b).

The method for producing a sulfonium salt compound according to this embodiment includes: Step (a) of subjecting, to dehydration condensation, the sulfoxide compound represented by the aforementioned general formula (V) and the naphthalene compound represented by the aforementioned general formula (VI); and Step (b) of producing the sulfonium salt compound represented by the aforementioned general formula (I) by reaction between a dehydrated condensate obtained above by the dehydration condensation in Step (a) and a salt compound or an acid compound represented by the aforementioned general formula $X^-Y^+$.

The dehydration condensation in Step (a) and the reaction in Step (b) between the dehydrated condensate obtained in Step (a) and the salt compound or acid compound can be carried out, for example, with reference to a publicly known method such as methods disclosed in J. Org. Chem., 55, 4222 (1990), J. Chem. Soc. Chem. Commun., 470 (1991), Chem. Pharm. Bull., 29, 3753 (1981), and J. Chem. Soc. Chem. Commun., 41 (1980). Specifically, Step (a) can be performed by subjecting the sulfoxide compound and the naphthalene compound to dehydration condensation, using a dehydrating agent exemplified below and a strong acid such as methanesulfonic acid, in the absence or presence of a solvent exemplified below. Further, Step (b) can be performed subsequently by reaction between the condensation reaction product obtained in Step (a) and the compound represented by $X^-Y^+$ in the presence of a solvent exemplified below.

From the viewpoint of improving the yield rate and the economic viewpoint, the aforementioned sulfoxide compound can be used, with respect to the naphthalene compound to be used, generally at a ratio of about 0.8 to 2 mole, preferably at a ratio of about 0.9 to 1.5 mole, more preferably at a ratio of about 1.0 to 1.2 mole.

In Step (a), the dehydration condensation reaction can be carried out in the presence of a dehydrating agent. Examples of the dehydrating agent include: inorganic compounds such as diphosphorus pentoxide, sodium sulfate, and magnesium sulfate; and organic compounds such as acetic anhydride, trifluoroacetic acid anhydride, propionic acid anhydride, phthalic acid anhydride, and methanesulfonic acid anhydride. The dehydrating agent is more preferably diphosphorus pentoxide. These dehydrating agents may be used individually, or two or more of them may be used in combination.

Such a dehydrating agent can be used, per mole of the aforementioned naphthalene compound to be used, generally at a ratio of about 0.3 to 5 mole, preferably at a ratio of about 0.4 to 3 mole, which is however not restrictive.

In Step (a), the dehydration condensation reaction can be carried out in the presence of a strong acid. Examples of the strong acid include methanesulfonic acid, ethanesulfonic acid, and sulfuric acid. The strong acid is more preferably methanesulfonic acid. These strong acids may be used individually, or two or more of them may be used in combination.

Further, the strong acids may be used in combination with the aforementioned dehydrating agent.

Such a strong acid can be used, per mole of the naphthalene compound to be used, generally at a ratio of about 1 to 25 mole, preferably at a ratio of about 2 to 15 mole, which is however not restrictive.

A solvent may be used or may be omitted in the aforementioned dehydration condensation reaction of the sulfoxide compound and the naphthalene compound in the presence of the dehydrating agent. In the case of using a solvent in this reaction, the solvent needs only to be inactive to the reactants. Specific examples of such a solvent include: chloroform; dichloromethane; ether solvents such as 1,4-dioxane, ethylene glycol dimethyl ether, diethylene glycol dimethyl ether, triethylene glycol dimethyl ether, and tetraethylene glycol dimethyl ether; nitrile solvents such as acetonitrile, propionitrile, and butyronitrile; amides such as N,N-dimethylformamide and N,N-dimethylacetamide; and sulfolane. These solvents can be used individually, or can be mixed for use. The reaction solvent can be used, with respect to 100 parts by weight of the naphthalene compound, generally in an amount of about 30 to 3000 parts by weight, preferably in an amount of about 50 to 2000 parts by weight.

Examples of the procedure in the dehydration condensation reaction include a procedure in which, while specific amounts of the naphthalene compound, the dehydrating agent, and the reaction solvent, etc., are mixed and stirred, a specific amount of the sulfoxide compound is added thereto, which is however not restrictive.

The dehydration condensation reaction is carried out at a reaction temperature of generally $-20°$ C. to $100°$ C., preferably $-10°$ C. to $80°$ C., more preferably $0°$ C. to $40°$ C.

In Step (b), the procedure in the aforementioned reaction between the dehydration condensation reaction product and the compound represented by $X^-Y^+$ (that is, salt exchange reaction) is not specifically limited. Examples of such a procedure include: (1) a procedure in which an aqueous solution is prepared by adding a specific amount of the compound represented by $X^-Y^+$ to a specific amount of water, and thereafter this aqueous solution is added to the reaction solution after the aforementioned dehydration condensation reaction, (2) a procedure in which an aqueous solution is prepared by adding a specific amount of the compound represented by $X^-Y^+$ to a specific amount of water, and thereafter the reaction solution after the aforementioned dehydration condensation reaction is added to this aqueous solution, (3) a procedure in which a specific amount of the compound represented by $X^-Y^+$ is added to the reaction solution after the aforementioned dehydration condensation reaction, (4) a procedure in which the reaction solution after the aforementioned dehydration condensation reaction is added to a specific amount of the compound represented by $X^-Y^+$, (5) a procedure in which an aqueous solution of the dehydration condensation reaction product is formed by adding the reaction solution after the aforementioned dehydration condensation reaction to a specific amount of water, and thereafter a specific amount of the compound represented by $X^-Y^+$ is added to this aqueous solution, and (6) a procedure in which an aqueous solution of the dehydration condensation reaction product is formed by adding the reaction solution after the aforementioned dehydration condensation reaction to a specific amount of water, and thereafter this aqueous solution is added to a specific amount of the compound represented by $X^-Y^+$. In the aforementioned reaction, organic solvents such as dichloromethane and chloroform may be further added.

The compound represented by $X^-Y^+$ can be used, per mole of the naphthalene compound used in Step (a), generally at a ratio of about 0.8 to 2 mole, preferably about 0.9 to 1.3 mole, which is however not restrictive. Use of the compound represented by $X^-Y^+$ at a ratio of 0.8 mole or more can sufficiently suppress the decrease in yield rate. Further, use of this compound at a ratio of 2 mole or less allows proper effects corresponding to the used amount to be sufficiently obtained, which is therefore more economical.

It should be noted that this compound represented by $X^-Y^+$ can be added in the form of an aqueous solution as mentioned above.

Further, there may be a case where a desired amount of the reaction product cannot be obtained when a specific amount of the dehydration condensation reaction product is reacted with the compound represented by $X^-Y^+$ (salt exchange reaction) by adding a specific amount of the compound represented by $X^-Y^+$. If this is because the compound represented by $X^-Y^+$ is insufficient and thus the salt exchange reaction has not been completed, the following procedure can be performed, for example. That is, water or an organic solvent such as dichloromethane and chloroform is added to the reaction solution, as needed, the reaction solution is then separated into an aqueous layer and an organic layer, and the compound represented by $X^-Y^+$ is further added to the resultant organic layer. Thereafter, the salt exchange reaction may be carried out again. In this procedure, the compound represented by $X^-Y^+$ is added in an amount, preferably in the range of 0.05 to 0.5 times the initially added amount, more preferably in the range of 0.05 to 0.2 times the amount.

In Step (b), the salt exchange reaction can be carried out at a reaction temperature of generally about −10 to 100° C., preferably about 0 to 60° C. When the reaction temperature is −10° C. or more, a sufficiently high reaction speed and a comparatively short reaction time can be achieved. Further, when the reaction temperature is 100° C. or less, side reactions can be reduced, as a result of which a decrease in purity and yield rate can be suppressed.

After the completion of the reaction, the thus obtained sulfonium salt compound can be isolated, for example, by carrying out a procedure in which a precipitated solid is separated by filtration, or a procedure in which, after the reaction product is extracted using an organic solvent such as monochlorobenzene, ethyl acetate, and dichloromethane, the organic solvent is distilled off. Further, the sulfonium salt compound can be refined, as needed, by a conventional method such as column chromatography, charcoal treatment, and recrystallization using a solvent such as ethyl acetate, dichloromethane, methyl-t-butyl ether, isopropyl ether, monochlorobenzene, n-heptane, n-hexane, methanol, and water.

The sulfonium salt compound of this embodiment has higher sensitivity to radiation, particularly to radiation in the i-line region, than conventional sulfonium salt compounds, and therefore can generate acid more efficiently than conventional sulfonium salt compounds by being decomposed by brief photoirradiation. Further, the sulfonium salt compound is dissolved well in a solvent to be used for resist materials, etc. In particular, the sulfonium salt compound has good solubility in PGMEA, which is a solvent generally used for chemically amplified resist materials.

Other than the radiation in the i-line region, examples of the radiation include far-ultraviolet ray radiation, broad radiation (three wavelength lines of g, h, and i), KrF (248 nm) excimer laser radiation, ArF (193 nm) excimer laser radiation, $F_2$ (157 nm) excimer laser radiation, electron beam radiation, and soft X-ray radiation.

Subsequently, a photoacid generator of the present embodiment is described.

The photoacid generator of this embodiment according to the present invention contains the sulfonium salt compound represented by the aforementioned chemical formula (I). This photoacid generator may contain a single kind of the sulfonium salt compound alone, or may contain two or more kinds including the aforementioned sulfonium salt compound and other sulfonium salt compounds in combination.

The photoacid generator can be used for chemically amplified resist materials. Such a chemically amplified resist material, for example, contains the photoacid generator, a resin, and a solvent capable of dissolving the photoacid generator and the resin.

Examples of the resin include a resin curable by polymerization with acid. When the chemically amplified resist material containing such a resin is applied and irradiated with radiation in a desired pattern, acid is generated in the irradiated portion, and this acid causes the irradiated portion to be cured. Then, the uncured portion is removed by a solvent capable of dissolving the resin, so that a so-called negative resist pattern is obtained. In this regard, examples of the resin include novolac epoxy resins, hydroxypolystyrene resins, and alkali-soluble phenol resins. Further, examples of the radiation include far-ultraviolet ray radiation, broad radiation (three wavelength lines of g, h, and i), KrF (248 nm) excimer laser radiation, ArF (193 nm) excimer laser radiation, $F_2$ (157 nm) excimer laser radiation, electron beam radiation, and soft X-ray radiation, other than the radiation in the i-line region.

In addition to above, examples of the resin include a resin into which a protecting group imparting insolubility in an alkali aqueous solution is introduced and which can be dissolved in the alkali aqueous solution by the protecting group being detached due to acid. When the chemically amplified resist material containing such a resin is applied and irradiated with the aforementioned radiation in a desired pattern, acid is generated in the irradiated portion, and this acid causes the detachment of the protecting group in the irradiated portion. Then, the irradiated portion is removed by the alkali aqueous solution, so that a so-called positive resist pattern is obtained. In this regard, examples of the resin include novolac resins, polyvinylphenol resins, acrylic resins, polynorbornene resins, and fluorine resins.

Further, the photoacid generator can be used for photocurable resin materials, other than the aforementioned chemically amplified resist material. Such a photocurable resin material, for example, contains: the photoacid generator; a monomer, oligomer, or polymer that is cured by polymerization with acid as mentioned above; and a solvent capable of dissolving the photoacid generator and the monomer, oligomer, or polymer therein. Then, when the photocurable resin material is applied and irradiated with the radiation light, acid is generated in the irradiated portion, and the irradiated portion is cured by this acid. In this regard, examples of the resin include epoxy resins, oxetane resins, and vinyl ether resins.

The sulfonium salt compound of this embodiment can be used for applications, for example, as a photoacid generator for chemically amplified resist materials that generates acid by irradiation with radiation, particularly with light beams, and uses the generated acid. Such a photoacid generator is suitably used, for example, for chemically amplified resist materials to be used for producing semiconductors, TFTs, color filters, micromachine parts, or the like.

Further, the sulfonium salt compound of this embodiment can be used for other applications that generate acid by irradiation with radiation, particularly with light beams, and uses the generated acid as a catalyst. Such a photoacid generator can be used for applications, for example, as a catalyst for polymerization reactions or crosslinking reactions. This photoacid generator enables a cured product having good properties to be obtained by surely polymerizing a curable compound within a short time.

As has been described above, the sulfonium salt compound of this embodiment represented by the aforementioned general formula (I) has a higher sensitivity to radiation, particularly radiation in the i-line region, than conventional sulfonium salt compounds, and therefore can generate acid more efficiently than conventional sulfonium salt compounds by being decomposed by brief photoirradiation. Further, this sulfonium salt compound is dissolved well in a solvent to be used for resist materials, etc. Particularly, the sulfonium salt compound has good solubility in PGMEA, which is a solvent generally used for chemically amplified resist materials.

Thus, the present invention provides a novel sulfonium salt compound that generates acid more efficiently than conventional sulfonium salt compounds and has good solubility in a solvent to be used for resist materials, etc., a method for producing the novel sulfonium salt compound, and a photoacid generator.

EXAMPLES

Hereinafter, the present invention is described in detail by way of examples. However, the present invention is not limited to these examples.

Example 1

Production of 1-(2,7-di-n-butoxynaphthyl)di-n-butylsulfonium di(1,1,2,2,3,3,4,4,4-nonafluorobutanesulfone)imide Diphosphorus pentoxide (1.7 g) and methanesulfonic acid (11.5 g) were put into a reaction container. Further, 2,7-dibutoxynaphthalene (8.2 g) and dibutylsulfoxide (6.3 g) were added thereto, which was stirred at room temperature for 16 hours. While the temperature within the reaction container was maintained at 0 to 10° C., a 20% NaOH aqueous solution (30 g) was added dropwise. After the dropwise addition, dichloromethane (80 g) was added thereto, which was allowed to stand still so as to be separated into layers. Thereafter, the aqueous layer was removed. Thus, an organic layer was obtained. The thus obtained organic layer was washed with deionized water (30 g), which was allowed to stand still so as to be separated into layers. Then, the aqueous layer was removed. Thus, a reaction solution of a condensation reaction product was obtained.

Deionized water (30 g) and potassium bis(nonafluorobutanesulfone)imide (18.6 g) were put into another reaction container. Further, the entire amount of the reaction solution obtained by the aforementioned procedure was added thereto, which was stirred at room temperature for 20 minutes. Thereafter, insoluble matter was filtrated. The thus obtained filtrate was allowed to stand still so as to be separated into layers, from which the aqueous layer was removed. Thus, an organic layer was obtained.

From the organic layer obtained by the aforementioned procedure, dichloromethane was distilled off. T-butylmethyl ether (MTBE) (17 g) and hexane (34 g) were added to the thus obtained concentrate at 50° C., which was crystallized. Thus, 18.8 g of white crystal of 1-(2,7-di-n-butoxynaphthyl)di-n-butylsulfonium di(1,1,2,2,3,3,4,4,4-nonafluorobutanesulfone)imide was obtained.

The following analysis results using $^1$H-NMR and LC-MS demonstrated that the thus obtained white crystal contained $R^1$, $R^2$, $R^3$, and $R^4$ each being a butyl group and $X^-$ being di(1,1,2,2,3,3,4,4,4-nonafluorobutanesulfone)imide anion, in the general formula (I).

$^1$H-NMR (400 MHz, DMSO-$d_6$, Internal standard material: tetramethylsilane): δ (ppm) 0.82 (t, J=7.3 Hz, 6H), 0.97 (t, J=7.3 Hz, 3H), 1.00 (t, J=7.3 Hz, 3H), 1.30-1.65 (m, 12H), 1.74-1.96 (m, 4H), 3.81-4.04 (m, 4H), 4.18 (t, J=6.6 Hz, 2H), 4.44 (t, J=6.6 Hz, 2H), 7.24 (dd, J=2.2 and 9.0 Hz, 1H), 7.50 (d, J=2.2 Hz, 1H), 7.57 (d, J=9.0 Hz, 1H), 8.01 (d, J=9.0 Hz, 1H), 8.36 (d, J=9.0 Hz, 1H)

MS (LC/ESI (+) Spectrum): $M^+$ 417
MS (LC/ESI (−) Spectrum): $M^-$ 580

Example 2

Production of 1-(2,7-di-n-butoxynaphthyl)dimethylsulfonium di(1,1,2,2,3,3,4,4,4-nonafluorobutanesulfone)imide 11.75 g of white crystal of 1-(2,7-di-n-butoxynaphthyl)dimethylsulfonium di(1,1,2,2,3,3,4,4,4-nonafluorobutanesulfone)imide was obtained in the same manner as Example 1, except that 2,7-dibutoxynaphthalene (5.45 g) as the naphthalene compound, dimethylsulfoxide (1.56 g) as the sulfoxide compound, and potassium bis(nonafluorobutanesulfone)imide (12.39 g) as the salt compound containing the $X^-$ represented by the aforementioned general formula (II) were used.

Further, the following analysis results were obtained in the same manner as in Example 1.

$^1$H-NMR (400 MHz, CDCl$_3$, Internal standard material: tetramethylsilane): δ (ppm) 0.99 (t, J=7.4 Hz, 3H), 1.06 (t, J=7.4 Hz, 3H), 1.50-1.61 (m, 4H), 1.83 (tq, J=7.4 and 7.4 Hz, 2H), 1.99 (tq, J=7.4 and 7.4 Hz, 2H), 3.41 (s, 6H), 4.18 (t, J=6.0 Hz, 2H), 4.39 (t, J=6.8 Hz, 2H), 7.16 (dd, J=2.6 and 8.9 Hz, 1H), 7.19 (d, J=9.4 Hz, 1H), 7.56 (d, J=2.6 Hz, 1H), 7.75 (d, J=9.4 Hz, 1H), 8.09 (d, J=8.9 Hz, 1H)

MS (LC/ESI (+) Spectrum): $M^+$ 333
MS (LC/ESI (−) Spectrum): $M^-$ 580

Example 3

Production of 1-(4,7-di-n-butoxynaphthyl)di-n-butylsulfonium di(1,1,2,2,3,3,4,4,4-nonafluorobutanesulfone)imide 6.33 g of white crystal of 1-(4,7-di-n-butoxynaphthyl)di-n-butylsulfonium di(1,1,2,2,3,3,4,4,4-nonafluorobutanesulfone)imide was obtained in the same manner as Example 1, except that 1,6-dibutoxynaphthalene (5.45 g) as the naphthalene compound, dibutylsulfoxide (3.89 g) as the sulfoxide compound, and potassium bis(nonafluorobutanesulfone)imide (12.01 g) as the salt compound containing the $X^-$ represented by the aforementioned general formula (II) were used.

Further, the following analysis results were obtained in the same manner as in Example 1.

$^1$H-NMR (400 MHz, DMSO-$d_6$, Internal standard material: tetramethylsilane): δ (ppm) 0.81 (t, J=7.4 Hz, 6H), 0.95 (t, J=7.4 Hz, 3H), 0.98 (t, J=7.2 Hz, 3H), 1.35 (tq, J=7.0 and 7.2 Hz, 4H), 1.42-1.59 (m, 8H), 1.78 (tt, J=6.4 and 7.2 Hz, 2H), 1.86 (tt, J=6.4 and 7.6 Hz, 2H), 3.75-3.81 (m, 2H), 3.84-3.91 (m, 2H), 4.17 (t, J=6.4 Hz, 2H), 4.30 (t, J=6.4 Hz, 2H), 7.22 (d, J=8.8 Hz, 1H), 7.36 (dd, J=2.0 and 8.7 Hz, 1H), 7.48 (d, J=2.0 Hz, 1H), 8.24 (d, J=8.8 Hz, 1H), 8.39 (d, J=8.7 Hz, 1H)

MS (LC/ESI (+) Spectrum): M$^+$ 417

MS (LC/ESI (−) Spectrum): M$^-$ 580

Example 4

Production of 1-(2,7-di-n-butoxynaphthyl)di-n-butylsulfonium 1,1,2,2,3,3-hexafluorotrimethylene sulfone imide Diphosphorus pentoxide (1.7 g) and methanesulfonic acid (11.5 g) were put into a reaction container. Further, 2,7-dibutoxynaphthalene (8.2 g) and dibutylsulfoxide (6.3 g) were added thereto, which was stirred at room temperature for 16 hours. While the temperature within the reaction container was maintained at 0 to 10° C., a 20% NaOH aqueous solution (30 g) was added dropwise. Thereafter, dichloromethane (80 g) was added thereto, which was allowed to stand still so as to be separated into layers. Then, the aqueous layer was removed. The thus obtained organic layer was washed with deionized water (30 g) and thereafter was separated into layers, from which the aqueous layer was removed. Thus, a reaction solution of a condensation reaction product was obtained.

Deionized water (30 g), 1,1,2,2,3,3-potassium hexafluorotrimethylene sulfone imide (11.9 g) as the salt compound containing the X$^-$ represented by the aforementioned general formula (III), and the entire amount of the reaction solution obtained by the aforementioned procedure were added to another reaction container, which was stirred at room temperature for 20 minutes. Thereafter, insoluble matter was filtrated. The thus obtained filtrate was allowed to stand still so as to be separated into layers, from which the aqueous layer was removed. Thus, an organic layer was obtained.

From the organic layer obtained by the aforementioned procedure, dichloromethane was distilled off. The thus obtained concentrate was refined by column chromatography, from which the solvent was thereafter distilled off under reduced pressure, followed by drying. Thus, 12.0 g of white crystal of 1-(2,7-di-n-butoxynaphthyl)di-n-butylsulfonium 1,1,2,2,3,3-hexafluorotrimethylene sulfone imide was obtained.

Further, the following analysis results were obtained in the same manner as in Example 1.

$^1$H-NMR (400 MHz, DMSO-$d_6$, Internal standard material: tetramethylsilane): δ (ppm) 0.84 (t, J=7.3 Hz, 6H), 0.97-1.09 (m, 6H), 1.35-1.72 (m, 12H), 1.81-1.97 (m, 4H), 3.75-3.84 (m, 2H), 3.96-4.07 (m, 2H), 4.16 (t, J=6.1 Hz, 2H), 4.37 (t, J=7.0 Hz, 2H), 7.14-7.27 (m, 2H), 7.52 (s, 1H), 7.78 (d, J=9.0 Hz, 1H), 8.13 (d, J=9.0 Hz, 1H)

MS (LC/ESI (+) Spectrum): M$^+$ 417

MS (LC/ESI (−) Spectrum): M$^-$ 292

Example 5

Production of 1-(2,4-di-n-butoxynaphthyl)di-n-butylsulfonium di(1,1,2,2,3,3,4,4,4-nonafluorobutanesulfone)imide 5.00 g of white crystal of 1-(2,4-di-n-butoxynaphthyl)di-n-butylsulfonium di(1,1,2,2,3,3,4,4,4-nonafluorobutanesulfone)imide was obtained in the same manner as Example 1, except that 1,3-dibutoxynaphthalene (1.77 g) as the naphthalene compound, dibutylsulfoxide (1.27 g) as the sulfoxide compound, and potassium bis(nonafluorobutanesulfone)imide (4.83 g) as the salt compound containing the X$^-$ represented by the aforementioned general formula (II) were used, and dichloromethane (45.50 g) was further used.

Further, the following analysis results were obtained in the same manner as in Example 1.

$^1$H-NMR (400 MHz, DMSO-$d_6$, Internal standard material: tetramethylsilane): δ (ppm) 0.78 (t, J=7.1 Hz, 6H), 1.00 (t, J=7.1 Hz, 6H), 1.32 (tq, J=6.4 and 7.1 Hz, 4H), 1.50 (tq, J=6.4 and 7.1 Hz, 4H), 1.54 (tt, J=7.1 and 7.1 Hz, 4H), 1.87-1.90 (m, 4H), 3.76-3.83 (m, 2H), 3.89-3.95 (m, 2H), 4.37 (t, J=6.2 Hz, 2H), 4.47 (t, J=6.2 Hz, 2H), 7.10 (s, 1H), 7.52 (dd, J=8.0 and 8.0 Hz, 1H), 7.77 (dd, J=8.0 and 8.0 Hz, 1H), 8.15 (d, J=8.0 Hz, 1H), 8.22 (d, J=8.0 Hz, 1H)

MS (LC/ESI (+) Spectrum): M$^+$ 417

MS (LC/ESI (−) Spectrum): M$^-$ 580

Example 6

Production of 1-(2,7-di-n-butoxynaphthyl)di-n-butylsulfonium 1,1,2,2,3,3,4,4,4-nonafluorobutanesulfonate Diphosphorus pentoxide (1.7 g) and methanesulfonic acid (11.5 g) were put into a reaction container. Further, 2,7-dibutoxynaphthalene (8.2 g) and dibutylsulfoxide (6.3 g) were added thereto, which was stirred at room temperature for 16 hours. While the temperature within the reaction container was maintained at 0 to 10° C., a 20% NaOH aqueous solution (30 g) was added dropwise. Thereafter, dichloromethane (80 g) was added thereto, which was allowed to stand still so as to be separated into layers. Then, the aqueous layer was removed. The thus obtained organic layer was washed with deionized water (30 g) and thereafter was separated into layers, from which the aqueous layer was removed. Thus, a reaction solution of a condensation reaction product was obtained.

Deionized water (30 g), potassium nonafluorobutanesulfonate (12.1 g) as the salt compound containing the X$^-$ represented by the aforementioned general formula (IV), and the entire amount of the reaction solution obtained by the aforementioned procedure were added to another reaction container, which was stirred at room temperature for 20 minutes. Thereafter, insoluble matter was filtrated. The thus obtained filtrate was allowed to stand still so as to be separated into layers, from which the aqueous layer was removed. Thus, an organic layer was obtained.

From the organic layer obtained by the aforementioned procedure, dichloromethane was distilled off. The thus obtained concentrate was refined by column chromatography, from which the solvent was thereafter distilled off under reduced pressure, followed by drying. Thus, 11.8 g of white crystal of 1-(2,7-di-n-butoxynaphthyl)di-n-butylsulfonium 1,1,2,2,3,3,4,4,4-nonafluorobutanesulfonate was obtained.

¹H-NMR (400 MHz, DMSO-$d_6$, Internal standard material: tetramethylsilane): δ (ppm) 0.82 (t, J=7.1 Hz, 6H), 0.98-1.10 (m, 6H), 1.35-1.75 (m, 12H), 1.84-1.96 (m, 4H), 3.95-4.09 (m, 4H), 4.16 (t, J=6.3 Hz, 2H), 4.35 (t, J=6.8 Hz, 2H), 7.14-7.22 (m, 2H), 7.58 (s, 1H), 7.77 (d, J=9.0 Hz, 1H), 8.10 (d, J=9.0 Hz, 1H)

MS (LC/ESI (+) Spectrum): M⁺ 417
MS (LC/ESI (−) Spectrum): M⁻ 299

Example 7

Production of 1-(4,8-di-n-butoxynaphthyl)di-n-butylsulfonium di(1,1,1-trifluoromethanesulfone)imide 21.81 g of white crystal (Example compound 7) of 1-(4,8-di-n-butoxynaphthyl)di-n-butylsulfonium di(1,1,1-trifluoromethanesulfone)imide was obtained in the same manner as Example 1, except that 1,5-dibutoxynaphthalene (10.90 g) as the naphthalene compound, dibutylsulfoxide (7.79 g) as the sulfoxide compound, and potassium bis(trifluoromethanesulfone)imide (12.77 g) as the salt compound containing the X⁻ represented by the aforementioned general formula (II) were used.

Further, the following analysis results were obtained in the same manner as in Example 1.

¹H-NMR (400 MHz, DMSO-$d_6$, Internal standard material: tetramethylsilane): δ (ppm) 0.87 (t, J=7.4 Hz, 6H), 1.00 (t, J=7.4 Hz, 3H), 1.02 (t, J=7.4 Hz, 3H), 1.34-1.46 (m, 4H), 1.46-1.67 (m, 8H), 1.83-2.00 (m, 4H), 3.79 (t, J=6.5 Hz, 4H), 4.30 (t, J=6.5 Hz, 2H), 4.33 (t, J=6.5 Hz, 2H), 7.32 (d, J=8.5 Hz, 1H), 7.37 (d, J=7.5 Hz, 1H), 7.63 (d, J=8.5 Hz, 1H), 7.96 (d, J=7.5 Hz, 1H), 8.26 (d, J=8.5 Hz, 1H)

MS (LC/ESI (+) Spectrum): M⁺ 417
MS (LC/ESI (−) Spectrum): M⁻ 280

Example 8

Production of 1-(4,8-di-n-butoxynaphthyl)di-n-butylsulfonium di(1,1,2,2,3,3,4,4,4-nonafluorobutanesulfone)imide 8.39 g of white crystal of 1-(4,8-di-n-butoxynaphthyl)di-n-butylsulfonium di(1,1,2,2,3,3,4,4,4-nonafluorobutanesulfone)imide was obtained in the same manner as Example 1, except that 1,5-dibutoxynaphthalene (8.17 g) as the naphthalene compound, dibutylsulfoxide (5.84 g) as the sulfoxide compound, and potassium bis(nonafluorobutanesulfone)imide (18.02 g) as the salt compound containing the X⁻ represented by the aforementioned general formula (II) were used.

Further, the following analysis results were obtained in the same manner as in Example 1.

¹H-NMR (400 MHz, DMSO-$d_6$, Internal standard material: tetramethylsilane): δ (ppm) 0.86 (t, J=7.4 Hz, 6H), 1.00 (t, J=7.4 Hz, 3H), 1.02 (t, J=7.4 Hz, 3H), 1.34-1.46 (m, 4H), 1.49-1.67 (m, 8H), 1.84-2.00 (m, 4H), 3.79 (t, J=6.5 Hz, 4H), 4.30 (t, J=6.5 Hz, 2H), 4.32 (t, J=6.5 Hz, 2H), 7.32 (d, J=8.5 Hz, 1H), 7.37 (d, J=7.5 Hz, 1H), 7.62 (d, J=8.5 Hz, 1H), 7.96 (d, J=7.5 Hz, 1H), 8.26 (d, J=8.5 Hz, 1H)

MS (LC/ESI (+) Spectrum): M⁺ 417
MS (LC/ESI (−) Spectrum): M⁻ 580

Example 9

Production of 1-(2,7-di-n-butoxynaphthyl)di-n-butylsulfonium di(1,1,1-trifluoromethanesulfone)imide 8.22 g of white crystal of 1-(2,7-di-n-butoxynaphthyl)di-n-butylsulfonium di(1,1,1-trifluoromethanesulfone)imide was obtained in the same manner as Example 1, except that potassium bis(trifluoromethanesulfone)imide (9.6 g) as the salt compound containing the X⁻ represented by the aforementioned general formula (II) was used.

Further, the following analysis results were obtained in the same manner as in Example 1.

¹H-NMR (400 MHz, DMSO-$d_6$, Internal standard material: tetramethylsilane): δ (ppm) 0.82 (t, J=7.3 Hz, 6H), 0.97 (t, J=7.3 Hz, 3H), 1.00 (t, J=7.3 Hz, 3H), 1.29-1.65 (m, 12H), 1.72-1.95 (m, 4H), 3.80-4.04 (m, 4H), 4.18 (t, J=6.6 Hz, 2H), 4.44 (t, J=6.6 Hz, 2H), 7.24 (dd, J=2.2 and 9.0 Hz, 1H), 7.50 (d, J=2.2 Hz, 1H), 7.57 (d, J=9.0 Hz, 1H), 8.01 (d, J=9.0 Hz, 1H), 8.37 (d, J=9.0 Hz, 1H)

MS (LC/ESI (+) Spectrum): M⁺ 417
MS (LC/ESI (−) Spectrum): M⁻ 280

Example 10

Production of 1-(4,7-di-n-butoxynaphthyl)di-n-butylsulfonium di(1,1,1-trifluoromethanesulfone)imide 5.34 g of white crystal of 1-(4,7-di-n-butoxynaphthyl)dibutylsulfonium di(1,1,1-trifluoromethanesulfone)imide was obtained in the same manner as Example 6, except that 1,6-dibutoxynaphthalene (8.2 g) as the naphthalene compound and potassium bis(trifluoromethanesulfone)imide (9.6 g) as the salt compound containing the X⁻ represented by the aforementioned general formula (II) were used.

Further, the following analysis results were obtained in the same manner as in Example 1.

¹H-NMR (400 MHz, DMSO-$d_6$, Internal standard material: tetramethylsilane): δ (ppm) 0.84 (t, J=7.4 Hz, 6H), 0.98 (t, J=7.4 Hz, 3H), 1.00 (t, J=7.2 Hz, 3H), 1.33-1.64 (m, 12H), 1.74-1.93 (m, 4H), 3.76-3.96 (m, 4H), 4.20 (t, J=6.4 Hz, 2H), 4.32 (t, J=6.4 Hz, 2H), 7.25 (d, J=8.8 Hz, 1H), 7.38 (dd, J=2.0 and 8.7 Hz, 1H), 7.51 (d, J=2.0 Hz, 1H), 8.27 (d, J=8.8 Hz, 1H), 8.42 (d, J=8.7 Hz, 1H)

MS (LC/ESI (+) Spectrum): M⁺ 417
MS (LC/ESI (−) Spectrum): M⁻ 280

Example 11

Production of 1-(2,7-di-n-octoxynaphthyl)dimethylsulfonium di(1,1,1-trifluoromethanesulfone)imide 17.11 g of white crystal of 1-(2,7-di-n-octoxynaphthyl)dimethylsulfonium di(1,1,1-trifluoromethanesulfone)imide was obtained in the same manner as Example 6, except that 2,7-dioctoxynaphthalene (11.54 g) as the naphthalene compound, dimethylsulfoxide (3.05 g) as the sulfoxide compound, and potassium bis(trifluoromethanesulfone)imide (9.6 g) as the salt compound containing the X⁻ represented by the aforementioned general formula (II) were used.

Further, the following analysis results were obtained in the same manner as in Example 1.

¹H-NMR (400 MHz, DMSO-$d_6$, Internal standard material: tetramethylsilane): δ (ppm) 0.82-0.93 (m, 6H), 1.18-1.53 (m, 20H), 1.75-1.87 (m, 2H), 1.88-2.00 (m, 2H), 3.39 (s, 6H), 4.17 (t, J=6.6 Hz, 2H), 4.42 (t, J=6.8 Hz, 2H), 7.21 (dd, J=2.4 and 9.0 Hz, 1H), 7.54 (d, J=9.3 Hz, 1H), 7.57 (d, J=2.4 Hz, 1H), 7.97 (d, J=9.0 Hz, 1H), 8.30 (d, J=9.3 Hz, 1H)

MS (LC/ESI (+) Spectrum): M⁺ 445
MS (LC/ESI (−) Spectrum): M⁻ 280

Example 12

Production of
1-(2,7-di-n-butoxynaphthyl)diisopropyl sulfonium
di(1,1,1-trifluoromethanesulfone)imide 4.11 g of white crystal of 1-(2,7-di-n-butoxynaphthyl) diisopropyl sulfonium di(1,1,1-trifluoromethanesulfone) imide was obtained in the same manner as Example 6, except that diisopropyl sulfoxide (5.24 g) as the sulfoxide compound and potassium bis(trifluoromethanesulfone)imide (9.6 g) as the salt compound containing the X$^-$ represented by the aforementioned general formula (II) were used.

Further, the following analysis results were obtained in the same manner as in Example 1.

$^1$H-NMR (400 MHz, DMSO-d$_6$, Internal standard material: tetramethylsilane): δ (ppm) 0.94 (t, J=7.6 Hz, 3H), 0.98 (t, J=7.3 Hz, 3H), 1.19 (d, J=6.8 Hz, 6H), 1.29-1.54 (m, 4H), 1.65 (d, J=6.8 Hz, 6H), 1.71-1.92 (m, 4H), 4.17 (t, J=6.2 Hz, 2H), 4.38 (t, J=6.8 Hz, 2H), 4.54-4.65 (m, 2H), 7.21 (dd, J=2.4 and 9.0 Hz, 1H), 7.51-7.56 (m, 2H), 7.98 (d, J=9.0 Hz, 1H), 8.34 (d, J=9.0 Hz, 1H)

MS (LC/ESI (+) Spectrum): M$^+$ 389
MS (LC/ESI (−) Spectrum): M$^-$ 280

Example 13

Production of
1-(2,7-di-n-butoxynaphthyl)diisopropyl sulfonium
di(1,1,2,2,3,3,4,4,4-nonafluorobutanesulfone)imide 5.13 g of white crystal of 1-(2,7-di-n-butoxynaphthyl) diisopropyl sulfonium di(1,1,2,2,3,3,4,4,4-nonafluorobutanesulfone)imide was obtained in the same manner as Example 6, except that diisopropyl sulfoxide (5.24 g) as the sulfoxide compound was used.

Further, the following analysis results were obtained in the same manner as in Example 1.

$^1$H-NMR (400 MHz, DMSO-d$_6$, Internal standard material: tetramethylsilane): δ (ppm) 0.96 (t, J=7.6 Hz, 3H), 0.99 (t, J=7.3 Hz, 3H), 1.19 (d, J=6.2 Hz, 6H), 1.30-1.55 (m, 4H), 1.66 (d, J=6.8 Hz, 6H), 1.71-1.92 (m, 4H), 4.17 (t, J=6.2 Hz, 2H), 4.39 (t, J=6.8 Hz, 2H), 4.54-4.66 (m, 2H), 7.22 (dd, J=2.4 and 8.8 Hz, 1H), 7.51-7.58 (m, 2H), 7.99 (d, J=8.8 Hz, 1H), 8.35 (d, J=8.8 Hz, 1H)

MS (LC/ESI (+) Spectrum): M$^+$ 389
MS (LC/ESI (−) Spectrum): M$^-$ 580

Comparative Example 1

Production of triphenylsulfonium
1,1,2,2,3,3-hexafluorotrimethylene imide

Dichloromethane (20 g) and triphenylsulfonium bromide (2.06 g) were put into a reaction container. Further, deionized water (10 g) and potassium 1,1,2,2,3,3-hexafluorotrimethylene sulfone imide (1.99 g) were added thereto, which was stirred at room temperature for 20 minutes. The reaction solution was allowed to stand still so as to be separated into layers, from which the aqueous layer was removed. Thus, an organic layer was obtained.

The obtained organic layer was filtrated, and the filtrate was washed with deionized water. Thereafter, the organic layer was fractionated. From the thus obtained organic layer, dichloromethane was distilled off. Thus, 3.14 g of white crystal of triphenylsulfonium 1,1,2,2,3,3-hexafluorotrimethylene imide was obtained.

$^1$H-NMR (400 MHz, CDCl$_3$, Internal standard material: tetramethylsilane): δ (ppm) 7.62-7.68 (m, 6H), 7.69-7.76 (m, 6H), 7.77-7.83 (m, 3H)

MS (LC/ESI (+) Spectrum): M$^+$ 263
MS (LC/ESI (−) Spectrum): M$^-$ 292

Comparative Example 2

Production of
1-(2,7-dimethoxynaphthyl)diphenylsulfonium
1,1,2,2,3,3-hexafluorotrimethylene sulfone imide 99.67 g of white crystal of 1-(2,7-dimethoxynaphthyl) diphenylsulfonium 1,1,2,2,3,3-hexafluorotrimethylene sulfone imide was obtained in the same manner as Example 1, except that 2,7-dimethoxy naphthalene (37.64 g) as the naphthalene compound, potassium 1,1,2,2,3,3-hexafluorotrimethylene sulfone imide (66.26 g) as the sulfoxide compound, and diphenyl sulfoxide (40.45 g) as the salt compound were used.

Further, the following analysis results were obtained in the same manner as in Example 1.

$^1$H-NMR (400 MHz, DMSO-d$_6$, Internal standard material: tetramethylsilane): δ (ppm) 3.80 (s, 3H), 3.95 (s, 3H), 7.29 (d, J=2.2 Hz, 1H), 7.31 (d, J=2.2 Hz, 1H), 7.55-7.89 (m, 11H), 8.09 (d, J=9.0 Hz, 1H), 8.51 (d, J=9.0 Hz, 1H)

MS (LC/ESI (+) Spectrum): M$^+$ 373
MS (LC/ESI (−) Spectrum): M$^-$ 292

Comparative Example 3

Production of
1-(2,7-di-n-butoxynaphthyl)di-n-butylsulfonium
hexafluorophosphate Diphosphorus pentoxide (1.1 g) and methanesulfonic acid (7.3 g) were put into a reaction container. 2,7-dibutoxynaphthalene (5.5 g) and dibutylsulfoxide (3.3 g) were added thereto, which was stirred at room temperature for 16 hours. Further, a 20% NaOH aqueous solution (19 g) was added dropwise. After the dropwise addition, dichloromethane (50 g) was added thereto, which was allowed to stand still so as to be separated into layers. Thereafter, the aqueous layer was removed. Thus, an organic layer was obtained. The thus obtained organic layer was washed with deionized water (19 g) and thereafter was separated into layers, from which the aqueous layer was removed. Thus, a reaction solution of a condensation reaction product was obtained.

Deionized water (19 g), potassium hexafluorophosphate (3.7 g), and the entire amount of the reaction solution obtained above were added to another reaction container, which was stirred at room temperature for 20 minutes. Thereafter, insoluble matter was filtrated. The thus obtained reaction solution was allowed to stand still so as to be separated into layers, from which the aqueous layer was removed. Thus, an organic layer was obtained.

From the obtained organic layer, dichloromethane was distilled off. The thus obtained concentrate was refined by column chromatography, from which the solvent was thereafter distilled off under reduced pressure, followed by drying. Thus, 4.8 g of white crystal of 1-(2,7-di-n-butoxynaphthyl)di-n-butylsulfonium hexafluorophosphate was obtained.

¹H-NMR (400 MHz, DMSO-d₆, Internal standard material: tetramethylsilane): δ (ppm) 0.84 (t, J=7.0 Hz, 6H), 1.01 (t, J=7.0 Hz, 3H), 1.06 (t, J=7.0 Hz, 3H), 1.37-1.49 (m, 6H), 1.57-1.69 (m, 6H), 1.86 (tq, J=7.0 and 7.0 Hz, 2H), 1.94 (tq, J=7.0 and 7.0 Hz, 2H), 3.73-3.78 (m, 2H), 3.96-4.03 (m, 2H), 4.17 (t, J=7.0 Hz, 2H), 4.37 (t, J=7.0 Hz, 2H), 7.16 (dd, J=2.0 and 9.0 Hz, 1H), 7.21 (d, J=9.0 Hz, 1H), 7.54 (d, J=2.0 Hz, 1H), 7.78 (d, J=9.0 Hz, 1H), 8.11 (d, J=9.0 Hz, 1H)

MS (LC/ESI (+) Spectrum): M⁺ 417
MS (LC/ESI (−) Spectrum): M⁻ 145

Comparative Example 4

Production of triphenylsulfonium di(1,1,2,2,3,3,4,4,4-nonafluorobutanesulfone)imide Dichloromethane (20 g) and triphenylsulfonium bromide (2.06 g) were put into a reaction container. Further, deionized water (10 g) and potassium di(1,1,2,2,3,3,4,4,4-nonafluorobutanesulfone)imide (3.72 g) were added thereto, which was stirred at room temperature for 20 minutes. The thus obtained reaction solution was allowed to stand still so as to be separated into layers, from which the aqueous layer was removed. Thus, an organic layer was obtained.

The obtained organic layer was filtrated, and the filtrate was washed with deionized water. Thereafter, the organic layer was fractionated. From the thus obtained organic layer, dichloromethane was distilled off. Thus, 4.86 g of white crystal of triphenylsulfonium di(1,1,2,2,3,3,4,4,4-nonafluorobutanesulfone)imide was obtained.

¹H-NMR (400 MHz, CDCl₃, Internal standard material: tetramethylsilane): δ (ppm) 7.63-7.68 (m, 6H), 7.68-7.74 (m, 6H), 7.75-7.81 (m, 3H)

MS (LC/ESI (+) Spectrum): M⁺ 263
MS (LC/ESI (−) Spectrum): M⁻ 580

Comparative Example 5

Production of 1-(2,7-di-n-butoxynaphthyl)diphenylsulfonium di(1,1,2,2,3,3,4,4,4-nonafluorobutanesulfone)imide 18.68 g of white crystal of 1-(2,7-di-n-butoxynaphthyl)diphenylsulfonium di(1,1,2,2,3,3,4,4,4-nonafluorobutanesulfone)imide was obtained in the same manner as Example 1, except that 2,7-dibutoxynaphthalene (8.17 g) as the naphthalene compound, diphenyl sulfoxide (6.07 g) as the sulfoxide compound, and potassium bis(nonafluorobutanesulfone)imide (18.58 g) as the salt compound containing the X⁻ represented by the aforementioned general formula (II) were used.

¹H-NMR (400 MHz, DMSO-d₆, Internal standard material: tetramethylsilane): δ (ppm) 0.76 (t, J=7.3 Hz, 6H), 0.96 (t, J=7.3 Hz, 3H), 0.92-1.06 (m, 2H), 1.18-1.28 (m, 2H), 1.42-1.55 (m, 2H), 1.72-1.82 (m, 2H), 4.10-4.23 (m, 4H), 7.29 (dd, J=2.2 and 9.2 Hz, 1H), 7.58 (d, J=9.2 Hz, 1H), 7.72-7.88 (m, 11H), 8.08 (d, J=9.2 Hz, 1H), 8.48 (d, J=9.2 Hz, 1H)

MS (LC/ESI (+) Spectrum): M⁺ 457
MS (LC/ESI (−) Spectrum): M⁻ 580

Solubility

The thus obtained sulfonium salt compounds were used as test compounds. PGMEA was added to 100 mg of each test compound, and the amount of PGMEA necessary for dissolving the test compound therein after the elapse of 30 minutes by repeating 30-second strong shaking at 20±5° C. every 5 minutes was measured. Here, "dissolving" means to reach the state where no insoluble matter can be observed by visual inspection, specifically, means that the resultant solution is clear, or a mixture in an arbitrary ratio becomes transparent. Table 1 below shows the amount of PGMEA (μL) necessary for dissolving the test compound. In Table 1 below, sulfonium salt compounds with an amount of PGMEA of 300 μL or less were evaluated as having desirable properties. Table 1 shows the results.

TABLE 1

| Test compound | PGMEA (μL) |
| --- | --- |
| Ex. 1 | 100 |
| Ex. 2 | 100 |
| Ex. 3 | 100 |
| Ex. 4 | 200 |
| Ex. 5 | 100 |
| Ex. 6 | 100 |
| Ex. 7 | 100 |
| Ex. 8 | 100 |
| Ex. 9 | 200 |
| Ex. 10 | 100 |
| Ex. 11 | 100 |
| Ex. 12 | 100 |
| Ex. 13 | 100 |
| C. Ex. 1 | 300 |
| C. Ex. 2 | 1400 |
| C. Ex. 3 | 1900 |
| C. Ex. 4 | 100 |
| C. Ex. 5 | 100 |

Measurement of Ultraviolet-Visible Absorption Spectrum

A $1 \times 10^{-4}$ mol/L acetonitrile solution of each test compound was prepared, and the molecular extinction coefficient at 365 nm in the ultraviolet-visible absorption spectrum was measured using an ultraviolet-visible spectrophotometer (UV-2400PC, manufactured by SHIMADZU CORPORATION). Table 2 shows the results. Considering that light would be transmitted to a deep portion of a thick film, the reference range of the molecular extinction coefficient at 365 nm (i-line) was set to 50 to 2000. The sulfonium compounds falling within this range were evaluated as having desirable properties.

TABLE 2

| Test compound | Molecular extinction coefficient (365 nm) |
| --- | --- |
| Ex. 1 | 580 |
| Ex. 2 | 480 |
| Ex. 3 | 810 |
| Ex. 4 | 700 |
| Ex. 5 | 100 |
| Ex. 6 | 690 |
| Ex. 7 | 570 |
| Ex. 8 | 620 |
| Ex. 9 | 560 |
| Ex. 10 | 940 |
| Ex. 11 | 440 |
| Ex. 12 | 880 |
| Ex. 13 | 1030 |
| C. Ex. 1 | 0 |
| C. Ex. 2 | 2010 |
| C. Ex. 3 | 490 |
| C. Ex. 4 | 0 |
| C. Ex. 5 | 2930 |

Evaluation of Decomposition and Acid Generation Amount by Photoirradiation

Using each test compound, a 0.02-mmol/g acetonitrile solution was prepared. 5.00 g of the thus prepared acetonitrile solution was put into a beaker, which was allowed to stand still under a handy UV lamp (SLUV-6, 365 nm), manufactured by AS ONE Corporation, so as to be exposed to light at 365 nm and 0.4 mW/cm² for 1200 seconds. The solution after the exposure was titrated with a 0.05N potassium hydroxide solution. A correction was performed by subtracting a value as a blank obtained by measuring (titrating) the solution before the photoirradiation in the same manner as above from the titration value (measured value) obtained above. Thus, the acid generation rate was determined by the following formula from a titration value (acid titration value) after the correction. Table 3 shows the results.

Acid generation rate (%)=[Acid titration value (mol)/ the theoretical number of moles of each compound (mol)]×100

TABLE 3

| Test compound | Exposure amount (mJ/cm²) | Acid generation rate (%) |
|---|---|---|
| Ex. 1 | 480 | 12 |
| Ex. 2 | 480 | 6 |
| Ex. 3 | 480 | 19 |
| Ex. 4 | 480 | 12 |
| Ex. 5 | 480 | 3 |
| Ex. 6 | 480 | 12 |
| Ex. 7 | 480 | 16 |
| Ex. 8 | 480 | 17 |
| Ex. 9 | 480 | 9 |
| Ex. 10 | 480 | 17 |
| Ex. 11 | 480 | 4 |
| Ex. 12 | 480 | 25 |
| Ex. 13 | 480 | 15 |
| C. Ex. 1 | 480 | 4 |
| C. Ex. 2 | 480 | 0 |
| C. Ex. 3 | 480 | 15 |
| C. Ex. 4 | 480 | 2 |
| C. Ex. 5 | 480 | 1 |

Table 1 to Table 3 above showed that the triphenylsulfonium compound (Comparative Example 1 and Comparative Example 4) conventionally used as a cation skeleton had a low molecular extinction coefficient (365 nm) of less than 50, which is the lower limit value of the aforementioned reference range, and a low acid generation efficiency of 2 to 4%. Further, the sulfonium compound having a naphthalene ring not satisfying requirements of the present invention as a cation skeleton (Comparative Examples 2 and 5) had a molecular extinction coefficient (365 nm) exceeding 2000, which is the upper limit value of the aforementioned reference range, and a low acid generation rate of 0 to 1%.

On the other hand, Examples 1, 3, 5, and 8 having the same anion skeleton and having a cation skeleton in which only the locations of the substituents of the naphthalene ring are different from one another had a molecular extinction coefficient (365 nm) falling within the aforementioned reference range (50 to 2000), and an acid generation rate of 3 to 19%. Further, Examples 1, 3, 5, and 8 had better molecular extinction coefficient (365 nm) and higher acid generation rate, as compared to Comparative Example 5 having the same anion skeleton and having a cation skeleton in which the type of the substituents of the naphthalene ring is different from these examples.

From the aforementioned results for molecular extinction coefficient (365 nm), acid generation rate, and solubility in PGMEA, it can be said that, as a cation skeleton to be contained in the sulfonium salt compound, a cation skeleton satisfying requirements of the present invention exerts more excellent actions and effects than a cation skeleton not satisfying requirements of the present invention.

On the other hand, when Comparative Example 3 and Examples 1, 4, 6, and 9 having the same cation skeleton and a different anion skeleton from one another are compared, comparable results were obtained for molecular extinction coefficient (365 nm) and acid generation rate. However, Comparative Example 3 having hexafluorophosphate anion that was conventionally used had an exceptionally low solubility in PGMEA, and thus a desired solubility was not obtained. From this result, it can be said that, as an anion skeleton to be contained in the sulfonium salt compound, an anion skeleton satisfying requirements of the present invention exerts more excellent actions and effects than an anion skeleton not satisfying requirements of the present invention.

From the aforementioned results, it can be said that the sulfonium salt compound according to the present invention and the photoacid generator containing the sulfonium salt in which the value of molecular extinction coefficient (365 nm) is reflected in the acid generation rate are capable of efficiently generating acid. Accordingly, it is inferred that a reaction time due to i-line photoirradiation at 365 nm will be much shortened. Further, good solubility in PGMEA, which is a solvent generally used for resist materials, is achieved.

INDUSTRIAL APPLICABILITY

The present invention can be used as a photoacid generator for chemically amplified resist materials, and is expected to be further used, for example, as a polymerization initiator used in combination with a curable resin that is cured by polymerization with acid.

What is claimed is:
1. A sulfonium salt compound represented by the following general formula (I):

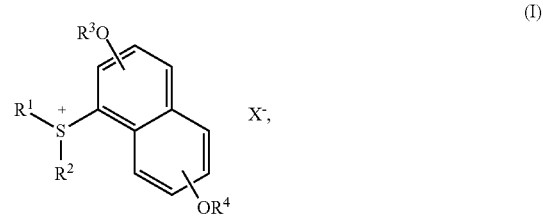

wherein $R^1$ and $R^2$ each denote the same or a different alkyl group having 1 to 18 carbon atoms, $R^3$ and $R^4$ each denote the same or a different alkyl group having 1 to 10 carbon atoms, and $X^-$ denotes a sulfone imide anion or a perfluoroalkanesulfonic acid anion represented by the formula (IV):

$$R^8\text{—}SO_3^- \tag{IV}$$

wherein $R^8$ denotes an alkyl group having 2 to 4 carbon atoms in which all hydrogen atoms are substituted by fluorine atoms, and wherein the substituents denoted by $R^3O$ and $R^4O$ are each located at an arbitrary position selected from the 2-position to the 8-position of the naphthyl group.

2. The sulfonium salt compound according to claim 1, wherein
$R^1$ and $R^2$ each denote the same or a different alkyl group having 1 to 8 carbon atoms, and
$R^3$ and $R^4$ each denote the same or a different alkyl group having 1 to 8 carbon atoms.

3. The sulfonium salt compound according to claim 1, wherein

X⁻ denotes a sulfone imide anion represented by the following general formula (II) or

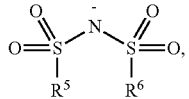
(II)

where $R^5$ and $R^6$ each denote the same or a different alkyl group having 1 to 6 carbon atoms in which at least one hydrogen atom is substituted by a fluorine atom; or

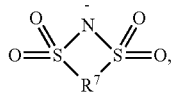
(III)

where $R^7$ denotes an alkylene group having 2 to 5 carbon atoms in which at least one hydrogen atom is substituted by a fluorine atom.

4. The sulfonium salt compound according to claim 3, wherein
   $R^5$ and $R^6$ each denote the same or a different alkyl group having 1 to 4 carbon atoms in which at least one hydrogen atom is substituted by a fluorine atom.

5. The sulfonium salt compound according to claim 3, wherein
   $R^7$ denotes an alkylene group having 3 carbon atoms in which at least one hydrogen atom is substituted by a fluorine atom.

6. A photoacid generator containing the sulfonium salt compound according to claim 1.

7. A method for producing a sulfonium salt compound, comprising:
   Step (a) of subjecting, to dehydration condensation, a sulfoxide compound represented by the following general formula (V):

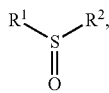
(V)

where $R^1$ and $R^2$ each denote the same or a different alkyl group having 1 to 18 carbon atoms, and a naphthalene compound represented by the following formula (VI):

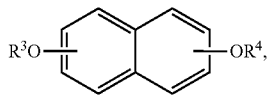
(VI)

where $R^3$ and $R^4$ each denote the same or a different alkyl group having 1 to 10 carbon atoms, wherein the substituents denoted by $R^3O$ and $R^4O$ are each located at an arbitrary position selected from the 2-position to the 8-position of the naphthyl group; and Step (b) of producing a sulfonium salt compound represented by the following general formula (I):

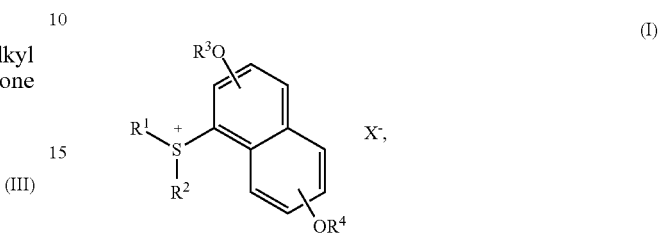
(I)

where $R^1$ and $R^2$ each denote the same substituent as defined in the aforementioned general formula (V), $R^3$ and $R^4$ each denote the same substituent as defined in the aforementioned general formula (VI), and X⁻ denotes the same substituent as defined in the general formula X⁻Y⁺, by reaction between a dehydrated condensate obtained by the dehydration condensation in Step (a) and a salt compound or an acid compound represented by a general formula X⁻Y⁺, where X⁻ is represented by the following general formula (II), (III), or (IV), and Y⁺ denotes an alkali metal ion or a hydrogen ion:

(II)

where $R^5$ and $R^6$ each denote the same or a different alkyl group having 1 to 6 carbon atoms in which at least one hydrogen atom is substituted by a fluorine atom;

(III)

where $R^7$ denotes an alkylene group having 2 to 5 carbon atoms in which at least one hydrogen atom is substituted by a fluorine atom; or

$$R^8-SO_3^- \quad (IV),$$

where $R^8$ denotes an alkyl group having 2 to 4 carbon atoms in which all hydrogen atoms are substituted by fluorine atoms.

* * * * *